United States Patent [19]

Lim et al.

[11] 4,074,039

[45] Feb. 14, 1978

[54] HYDROPHILIC N,N-DIETHYL ACRYLAMIDE COPOLYMERS

[75] Inventors: Drahoslav Lim, Stanford, Calif.; Jindrich Kopecek, Prague, Czechoslovakia; Hedvika Bazilova nee Sverinova, Nymburk, Czechoslovakia; Jiri Vacik, Prague, Czechoslovakia

[73] Assignee: Ceskoslovenska akademie ved, Prague, Czechoslovakia

[21] Appl. No.: 657,602

[22] Filed: Feb. 12, 1976

Related U.S. Application Data

[63] Continuation-in-part of Ser. No. 363,153, May 23, 1973, abandoned, which is a continuation-in-part of Ser. No. 124,567, March 15, 1971, abandoned.

[30] Foreign Application Priority Data

Mar. 26, 1970 Czechoslovakia ................... 2020/70

[51] Int. Cl.$^2$ ............................................. C08F 220/54
[52] U.S. Cl. ............................................ 526/303; 3/1; 3/1.4; 128/156; 260/29.6 TA; 424/81; 264/1; 351/160
[58] Field of Search ................................ 526/303, 306

[56] References Cited

U.S. PATENT DOCUMENTS 3,660,545   5/1972   Wichterle ................................ 264/1

FOREIGN PATENT DOCUMENTS 831,881   4/1960   United Kingdom ................. 526/303

*Primary Examiner*—Stanford M. Levin

[57] ABSTRACT

There is disclosed a hydrophilic gel suitable for exposure to repeated long-term contact with live tissues or mucous membranes and consisting of macromolecules obtained by polymerizing a mixture of at least two copolymerizable units and a crosslinking agent. The mixture consists of from 52 to 99.5 parts by weight of N,N-diethylacrylamide, 43 to 0.1 parts by weight of a member selected from the group consisting of N,N-dialkyl acrylamide, N-alkyl methacrylamide, nitriles of acrylic and methacrylic acids and from 5 to 0.4 parts by of a divinylic monomer selected from the group consisting of diesters of acrylic acid and methacrylic acid, and methylene or ethylene-bis-methacrylamide or acrylamide.

10 Claims, No Drawings

HYDROPHILIC N,N-DIETHYL ACRYLAMIDE COPOLYMERS

RELATED APPLICATIONS

This application is a continuation-in-part of patent application Ser. No. 363,153, filed May 23, 1973, which application is a continuation-in-part of application Ser. No. 124,567, filed Mar. 15, 1971, both now abandoned. Reference is made to the prior applications for additional information, explanation and disclosure if necessary and such is hereby incorporated by reference, herein, as if more fully set forth.

The present invention relates to a method of manufacturing articles suitable for exposure to repeated or long-term contact with living tissues or mucous membranes. More particularly, the invention concerns a method of polymerizing in situ, non-ionic, monoolefinic hydrogels.

Hydrogels containing, as a hydrophilic component, chemical units having N-monoalkylmethacrylamide groups are known. Such hydrogels are suitable for manufacturing articles to be exposed to repeated and long-term contact with live tissues or mucous membranes, such as, for example in the manufacture of implants, endoprostheses or parts thereof and the like (see Czechoslovak Pat. No. 117 113). However, even though such hydrogels are generally satisfactory, they still present some disadvantages with respect to chemical stability and biological compatibility.

U.S. Pat. No. 2,680,110 describes as emulsion polymerization process that inherently produces a product distinct from one produced by solution or block polymerization. That process produces an aqueous dispersion containing free particles of polymer dispersed therein. The polymeric product thus produced does not therefore take the shape of the mold or vessel in which the polymerization process is carried out. The patent teaches a solvent soluble polymer which is cross-linked by heat subsequent to the polymerization.

In U.S. Pat. No. 2,893,970 there is disclosed a suspension polymerization to produce a product of small granular size, which product is thereafter further reacted with a polyester or a polyhydrocarbon. The method is not carried out in a vessel which has the shape of the product for which the polymeric composition is intended.

According to U.S. Pat. No. Re. 26,934 there is taught the preparation of chromatographic materials that must of necessity be used in a powdery form.

Materials generally known as hydrogels but which contain only unsubstituted acrylamide as the main monomer component thereof are unstable against attack by hydrolytic agents and as such have found limited utility in the prosthetic art.

Therefore, it is an object of the present invention to overcome the aforementioned disadvantages and to significantly improve the method of manufacturing articles suitable for exposure to repeated and long-term contact with live tissues and mucous membranes.

Now it has surprisingly been found that N,N-dialkylacrylamides because of their chemical stability and biological compatibility fully meet the respective requirements and provide hydrogels having both good physical and good mechanical characteristics.

It is an object of the instant invention to provide for an improved hydrogel monomeric materials to form polymeric materials directly useful as prosthetic devices.

It is another object of the invention to carry out the polymerization either in the presence or absence of a solvent.

It is a further object of the invention to carry out the process in the presence of radical initiators in a mold having the shape of the final implant or prosthetic device.

It is still a further object of this invention to avoid one or more drawbacks of the prior art.

These and other objects will become more apparent as the description proceeds.

According to the present invention there is provided a hydrophilic gel suitable for exposure to repeated long-term contact with live tissues or mucous membranes and consisting of macromolecules obtained by polymerizing a mixture of at least two copolymerizable units and crosslinking agent. The mixture consists of from 52 to 99.5 parts by weight of N,N-diethylacrylamide, 43 to 0.1 parts by weight of a member selected from the group consisting of N,N-dialkyl acrylamide, N-alkyl methacrylamide, nitriles of acrylic and methacrylic acids and from 5 to 0.4 parts by weight of a divinylic monomer selected from the group consisting of diesters of acrylic acid and methacrylic acid, and methylene or ethylene -bis-methacrylamide or acrylamide.

The alkyl groups of the N,N-dialkylacrylamide can be substituted by at least one radical selected from the group consisting of hydroxyl, polyhydroxyalkyl and amine radicals, as in N,N-dihydroxy ethyl acrylamide and have from 1 to 6 carbons. The term acrylamide as used herein, is intended to include methacrylamide. The alkyl groups preferably have one or two carbons.

The above polymerization process may be carried out, as aforesaid, either in the absence of any solvent or in the presence of a solvent such as a $C_{1-5}$ alkanol, DMF(dimethylformamide), DFS(dimethylsulfoxide), glycol monoethylether, pyridine, benzene and the like and in the presence of a free radical initiator.

The term N-substituted as used herein refers to N-mono-substituted, where the substituent is $C_{1-6}$ and can contain OH(1-3), amino(1-3) or a combination thereof.

The amount of the cross-linking agent which can be employed depends upon the desired degree of cross-linking. It is generally employed in an amount greater than the amount of bifunctional monomer and is also dependent on the type thereof as well as on its ability to form, under the given conditions, together with corresponding monomers, a cross-linked polymer. It is to be understood that in order to get the desired result it is necessary to add a larger amount of a less efficient cross-linking agent than of a more efficient one. The cross-linking agent can be used in amounts of .4 to 5% by weight of the mixture of monomers.

As hereinbefore set forth, suitable cross-linking agents include diesters or diamides of acrylic acid and methacrylic acid, as for example, glycol dimethacrylate, triethylene glycol dimethacrylate, diethylene glycol dimethacrylate, N,N-methylene-bis-acrylamide, methylene-bis-methacrylamide, ethylene - bis - acrylamide or methacrylamide, and the like.

Various dialkylacrylamides can be copolymerized with one another or together with other types of monomers, such as methacrylonitrile, acrylonitrile, acrylamide, N-substituted or disubstituted methacrylamides, N-monosubstituted acrylamides and the like. When using N,N-dialkylmethacrylamide as co-monomer, the amount of N,N-dialkylacrylamide has to substantially exceed the amount of the former, since dialkylmethacrylamides themselves are not capable of polymerization.

To initiate the polymerization, any of the known initiators for free radical polymerization can be used. These include various peroxides, peroxosulfates, substituted azo-compounds and the like. They are preferably employed in amounts of 0.01 to 2% by weight, although the amount used is not critical.

The polymerization is generally carried out at temperatures of 20° to 85° C, preferably at temperatures of 40° to 60° C. Various additives, such as chain regulators and the like may be employed if desired.

In a most preferred embodiment the polymerization process will be such that there occurs a copolymerization of monovinylic compounds and a divinylic compound, in the presence of a solvent, in a mold, such that the mold serves as the polymerization vessel and the final product, made in situ, has the shape of the mold within which it has been polymerized.

The following Examples are given as illustrative only without, however, limiting the invention to the specific details thereof. All parts, proportions and percentages therein as well as in the appended claims are by weight unless specified otherwise.

EXAMPLE 1

The mixture of 60% by weight of N,N-diethyl acrylamide, 38.9% by weight of N,N-dihydroxyethyl acrylamide, 1% by weight of triethylene glycol dimethacrylate and 0.1% by weight of benzoyl peroxide was dissolved in water to produce a solution containing 70% by weight solute and bubbled for 15 minutes with catalytically purified nitrogen. Subsequently, the mixture was transferred under an inert atmosphere into a polypropylenic mold and heated therein to 70° C for 10 hours. The transparent elastic gel obtained perfectly follows all of the contours of the mold used and could thereafter be used, after washing with water, placing in a physiological solution and sterilization, as a subcutaneous implantant for removing deformations in face surgery.

EXAMPLE 2

The mixture of 55% by weight of N,N-diethyl acrylamide, 44.25% by weight of N,N-dipropyl acrylamide, 0.7% by weight of glycol dimethacrylate and 0.05% by weight of azo-bis-isobutryonitrile was dissolved in n-butnaol to produce a solution containing 80% by weight of solute and heated to 60° C for 8 hours. A gel similar to that of Example 1 was obtained.

EXAMPLE 3

The mixture of 72% by weight of N, N-diethyl acrylamide, 26.75%, by weight of methacrylonitrile, 1.2% by weight of methylene-bis-acrylamide and 0.05% by weight of methyl-azo-bis-isobutyrate was dissolved in water to produce a solution containing 80% by weight of solute. The solution was bubbled through with pure nitrogen and polymerized for 7 hours in a rotating glass tube coated with teflon and heated in an air-oven to 60° C. After removal from the mold, the polymer was washed with water for 4 weeks and then placed in physiological saline solution. After sterilization the shaped polymer could be used in a substitute for tubular organs. In order to improve the mechanical properties of the polymer it is possible to reinforce the prostheses prepared according to this Example with a polyester matting.

EXAMPLE 4

The mixture of 58% by weight of N,N-diethyl acrylamide, 41.55% by weight of 2-hydroxypropyl methacrylamide, 0.4% by weight of ethylene-bis-methacrylamide and 0.05% by weight of diisopropyl percarbonate was dissolved in n-butanol to produce a solution containing 80% by weight of solute and was heated to 60° C for several hours. The result was a hydrogel of good physical properties suitable for use as a substitute or replacement for the peritoneum or hernia membranes.

EXAMPLE 5

The mixture of 73% by weight of N,N-diethyl acrylamide, 26.4% by weight of N,N-dimethyl methacrylamide, 0.5% by weight of trimethylolpropane trimethacrylate and 0.1% by weight azo-bis-isobutyronitrile was dissolved in water to produce a solution containing 80% by weight of solute and was heated to 70° for several hours. The result was a hydrogel of good physical properties.

EXAMPLE 6

The mixture of 68% by weight of N,N-diethyl acrylamide, 31.75% by weight of acrylonitrile, 0.2% by weight of diglycol dimethacrylate and 0.05% by weight of diisopropyl percarbonate was dissolved in water to produce a solution containing 60% by weight of solute and was heated to 60° C for 10 hours. The result was a hydrogel of good physical properties.

EXAMPLE 7

The mixture of 52% by weight of N,N-diethyl acrylamide, 47% by weight of N,N-dimethylol acrylamide, 0.9% by weight of methylene-bis-methacrylamide and 0.1% by weight of benzoyl peroxide was dissolved in ethanol to produce a solution containing 80% by weight of solute and was heated to 60° C for several hours. The result was a hydrogel of good physical properties.

EXAMPLE 8

The mixture of 55% by weight of N,N-diethyl acrylamide, 44.85% by weight of N-ethyl methacrylamide, 0.1% by weight of glycol dimethacrylate and 0.05% by weight of azo-bis-isobutyronitrile was dissolved in ethanol to produce a solution containing 80% by weight of solute and was heated to 60° C for 10 hours. The result was a hydrogel of good physical properties.

EXAMPLE 9

The mixture of 65% by weight of N,N-diethyl acrylamide, 14.65% by weight of N-hydroxethyl methacrylamide, 20% by weight of methacrylonitrile, 0.3% by weight of triethyleneglycol dimethacrylate and 0.05% by weight azo-bis-isobutyronitrile was dissolved in n-butanol to produce a solution containing 80% by weight of solute and was heated to 70° C for 7 hours. The result was a hydrogel of good physical properties.

EXAMPLE 10

The mixture of 53% by weight of N,N-diethyl acrylamide, 45.9% by weight of N-methyl methacrylamide, 1% by weight of diethylene glycol dimethyacrylate and 0.1% by weight of diisopropyl percarbonate, after having first been bubbled through with nitrogen and polymerized for 2 hours at 50° C and then for 6 hours at 60°

C, in a mold made of polypropylene. The resulting polymer can be mechanically worked up into various shapes, e.g. suitable for use as a vein or artery connection or replacement, then washed for several weeks with water and placed in a physiological solution. After sterilization, the blood vessel connection or replacement is ready for implanation.

EXAMPLE 11

The mixture of 95% by weight of N,N-diethyl acrylamide, 4.9% by weight of ethylene-bis-methacrylamide and 0.1% by weight of benzoyl peroxide, after having first been bubbled through with nitrogen, was polymerized for 10 hours at 70° C in a steel mold coated with Teflon and provided with spacing inserts made of silicone rubber. The membrane thereby produced was washed with water, physiological solution and sterilized for half an hour at 120° C. It may be used as a permeable cover for coating burns.

EXAMPLE 12

Biological Tolerance

The biological tolerance of the polymers of the invention was studied by subcutaneous implanation of such a polymer (e.g. of poly N,N-diethylacrylamide) in 50 rats and 5 pigs. Samples for testing were taken in the $1^{st}$, $2^{nd}$, $3^{rd}$, $4^{th}$ weeks and in the $2^{nd}$, $3^{rd}$, $4^{th}$, $5^{th}$, $6^{th}$ and $12^{th}$ month after implanation. The polymer samples were encapsulated with a ligament tissue capsule consisting of colored collagenous fibers and a few fibrocytes, which are embedded in the basic substances which may also be colored with alcian blue and give a positive reaction for glycoproteins. The collageneous fibers are arranged parallel to the implant surface.

Large multinuclear cells are not found in the neighborhood of the implant. The reaction for calcium is negative. In view of the above tests the biological tolerance of the studied polymers is found to be good.

The above synopsis of the biological tolerance of the polymer of the invention is described in greater detail in co-pending patent application serial number 363,153. Reference to the co-pending case is made in order to eliminate the need to repeat herein the details and is not an omission of the description of the biological tolerance of the polymer of the invention.

What is claimed is:

1. A hydrophilic gel for use in exposure to repeated or long term contact with live tissues or mucous membranes and consisting of marcomolecules obtained by polymerizing a mixture consisting of 43 to 0.1 parts by weight of a monomer selected from the group consisting of N-(2-hydroxypropyl) methacrylamide, N,N-dihydroxy ethylacrylamide, N-methyl methacrylamide, N-ethyl methacrylamide, acrylonitrile and methacrylonitrile, 52 to 99.5 parts by weight of N,N-diethyl acrylamide and 5 to 0.4 parts by weight of a crosslinking divinylic monomer selected from the group consisting of glycol dimethacrylate, diethylene glycol dimethacrylate, triethylene glycol dimethacrylate, methylene-bis-acrylamide and ethylene-bis- methacryl-amide in the presence of a free radical initiator.

2. The hydrophilic gel of claim 1, wherein said monomer is N,N-dihydroxy ethylacrylamide.

3. The hydrophilic gel of claim 1, wherein said monomer is methacrylonitrile.

4. The hydrophilic gel of claim 1, wherein said monomer is N-(2-hydroxypropyl) methacrylamide.

5. The hydrophilic gel of claim 1, wherein said monomer is acrylonitrile.

6. The hydrophilic gel of claim 1, wherein said monomer is N-ethyl methacrylamide.

7. The hydrophilic gel of claim 1, wherein said monomer is N-methyl methacrylamide.

8. The hydrophilic gel of claim 1, wherein said divinylic monomer is tri-glycol dimethacrylate.

9. The hydrophilic gel of claim 1, wherein said divinylic monomer is methylene-bis-acrylamide.

10. A hydrophilic gel for use in exposure to repeated or long term contact with live tissues or mucous membranes and consisting of macromolecules obtained by polymerizing a mixture consisting of 43 to 0.1 parts by weight of a monomer selected from the group consisting of N,N-dialkyl methacrylamide, N,N-dialkyl acrylamide, N-alkyl methacrylamide, acrylonitrile and methacrylonitrile, 52 to 99.5 parts by weight of N,N-diethyl acrylamide and 5 to 0.4 parts by weight of a crosslinking divinylic monomer selected from the group consisting of glycol dimethacrylate, triethylene glycol dimethacrylate, diethylene glycol dimethacrylate, and methylene or ethylene-bis-acrylamide or methacrylamide, wherein the alkyl moiety has from 1 to 6 carbons, except that in N,N-dialkyl acrylamide the alkyl group is other than ethyl, and wherein the alkyl moiety of said dialkyl methacrylamide and acrylamide may be substituted with at least one radical selected from the group consisting of hydroxyl, polyhydroxyalkyl and amine and the alkyl moiety of said alkyl methacrylamide may be substituted with a hydroxyl group, in the presence of a free radical initiator at a temperature of 20° to 85° C. for at least 7 hours.

* * * * *